(12) United States Patent
Massaro

(10) Patent No.: US 11,653,637 B2
(45) Date of Patent: May 23, 2023

(54) INSECT REARING CONTAINERS

(71) Applicant: Verily Life Sciences LLC, South San Francisco, CA (US)

(72) Inventor: Peter Massaro, San Carlos, CA (US)

(73) Assignee: VERILY LIFE SCIENCES LLC, South San Francisco, CA (US)

(*) Notice: Subject to any disclaimer, the term of this patent is extended or adjusted under 35 U.S.C. 154(b) by 733 days.

(21) Appl. No.: 16/227,860

(22) Filed: Dec. 20, 2018

(65) Prior Publication Data
US 2019/0191677 A1    Jun. 27, 2019

Related U.S. Application Data

(60) Provisional application No. 62/608,876, filed on Dec. 21, 2017.

(51) Int. Cl.
*A01K 67/033*      (2006.01)
*A01K 1/03*      (2006.01)

(52) U.S. Cl.
CPC ............ *A01K 67/033* (2013.01); *A01K 1/031* (2013.01)

(58) Field of Classification Search
CPC .............................. A01K 1/031; A01K 67/033
See application file for complete search history.

(56) References Cited

U.S. PATENT DOCUMENTS

| | | | |
|---|---|---|---|
| 3,653,358 A | 4/1972 | Fremont | |
| 4,192,443 A * | 3/1980 | McLaren | B65D 5/48004 229/120.16 |
| 4,279,217 A | 7/1981 | Behringer | |
| 4,826,012 A * | 5/1989 | Kosanovich | B65D 5/48038 206/499 |
| 5,178,094 A | 1/1993 | Carr et al. | |
| 5,351,643 A | 10/1994 | Hughes | |
| 5,359,808 A * | 11/1994 | Fitsakis | A01M 1/2016 43/132.1 |
| 5,709,167 A * | 1/1998 | Kelley | A01K 39/014 119/61.5 |
| 10,306,875 B1 * | 6/2019 | Massaro | A01K 67/033 |
| 2003/0047142 A1 * | 3/2003 | Cohen | A01K 67/033 119/6.5 |

(Continued)

FOREIGN PATENT DOCUMENTS

| | | |
|---|---|---|
| KR | 20090002991 | 1/2009 |
| WO | 2012115959 | 8/2012 |

OTHER PUBLICATIONS

PCT/US2018/066824, "International Search Report and Written Opinion", dated Mar. 11, 2019, 13 pages.

(Continued)

*Primary Examiner* — Monica L Perry
(74) *Attorney, Agent, or Firm* — Kilpatrick Townsend & Stockton LLP

(57) ABSTRACT

An example insect rearing system a vessel comprising at least one interior surface defining a volume; a liner comprising a liner material, the liner having a shape corresponding to a shape of the interior surface, the liner configured to be disposed within the volume to establish a cavity within which water, insect larvae, and insect larvae food may be disposed and maintained; and wherein the vessel defines an opening configured to receive the liner and to allow the liner to substantially conform to the shape of the interior surface.

34 Claims, 10 Drawing Sheets

(56) References Cited

U.S. PATENT DOCUMENTS

| | | |
|---|---|---|
| 2006/0016120 A1* | 1/2006 | Masters .................. A01M 1/14 |
| | | 43/107 |
| 2006/0266292 A1 | 11/2006 | Duckworth |
| 2007/0251858 A1* | 11/2007 | Martinez ................ B65D 77/02 |
| | | 206/703 |
| 2007/0257041 A1* | 11/2007 | Bramlage .............. A45C 13/02 |
| | | 220/507 |
| 2013/0319334 A1 | 12/2013 | Newton et al. |
| 2014/0069928 A1 | 3/2014 | Weng |
| 2017/0265443 A1 | 9/2017 | Winston, III et al. |
| 2018/0168133 A1* | 6/2018 | Taylor .................. A01K 63/065 |

OTHER PUBLICATIONS

Leppla, "The basics of quality control for insect rearing", Principles and procedures for rearing high quality insects, Mississippi State University, Mississippi State (2009): 289-306.

* cited by examiner

INSECT REARING CONTAINERS

CROSS-REFERENCE TO RELATED APPLICATIONS

This application claims priority to U.S. Provisional Application No. 62/608,876, filed Dec. 21, 2017, entitled "Insect Rearing Containers," which is hereby incorporated by reference in its entirety herein.

FIELD

The present disclosure relates generally to the mass-rearing of insects. More specifically, but not by way of limitation, this disclosure relates to insect rearing containers.

BACKGROUND

The mass-rearing of insect larvae can be very labor intensive. A lab technician may manually add a number of eggs or insect larvae to a plastic tray and determine the amount of food and water to add into the tray for the insect larvae. The lab technician may hand carry the plastic tray to a storage area to store the plastic tray. Periodically, the lab technician may perform observations on the insect larvae in the plastic tray or add food and water as needed. After the insects are released, the plastic trays can be cleaned and sterilized before being re-used. The cleaning processes can be labor intensive and include a contamination risk in subsequent uses of the tray.

SUMMARY

Various examples are described for insect rearing containers. One example insect rearing system includes a vessel comprising at least one interior surface defining a volume; a liner comprising a liner material, the liner having a shape corresponding to a shape of the interior surface, the liner configured to be disposed within the volume to establish a cavity within which water, insect larvae, and insect larvae food may be disposed and maintained; and wherein the vessel defines an opening configured to receive the liner and to allow the liner to substantially conform to the shape of the interior surface.

One example method includes providing a vessel comprising at least one interior surface defining a volume; forming a liner comprising a liner material within the volume and over the interior surface, the liner having a shape corresponding to a shape of the interior surface and establishing a cavity within which water, insect larvae, and insect larvae food may be disposed and maintained; and wherein the vessel defines an opening configured to receive the liner and to allow the liner to substantially conform to the shape of the interior surface.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
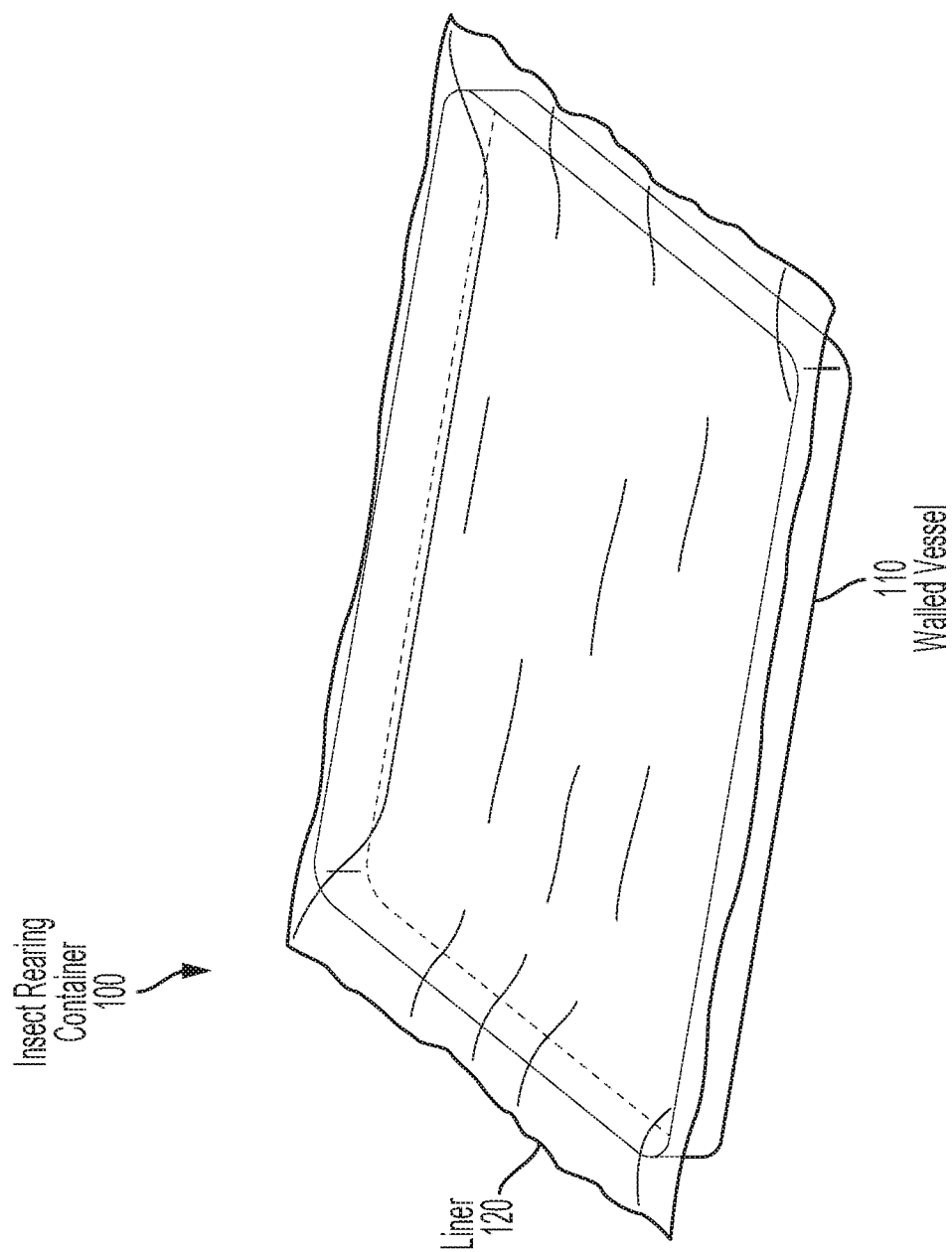
FIG. 1 shows an example insect rearing container.

Examples are described herein in the context of insect rearing containers. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

Mass rearing insects in a controlled environment can involve harvesting eggs laid by captive adult insects, hatching eggs into larvae, which are then moved into larvae rearing containers. However, because large quantities of larvae may be generated at each generation, and time to mature from larvae to pupae may be only a few days, larvae rearing containers must be emptied and either replaced or cleaned before a new population of larvae may be introduced. Absent such procedures, the new larvae may be exposed to any pathogens, waste products, or other contaminants left over from the prior population. However, cleaning rearing containers can be a time consuming and costly process, and if containers are not sufficiently cleaned, or if residual cleaning products are left in the container, larvae introduced into the container may be contaminated or killed.

To address these and other problems, an example insect rearing container includes a vessel and a liner laid within the vessel. The liner is overlaid on one or more dividers within the vessel. The liner rests over the dividers forming multiple discrete cavities between the dividers to allow for multiple different populations of insect larvae, such as mosquito larvae, to be raised in a single vessel. The distinct larvae populations may all be introduced to their respective cavities at substantially the same time, or they may be staggered, such as over the course of several days. By staggering larvae populations over time, a continuous rotation may be established, where pupae are retrieved from the container, while a new population of insect larvae is introduced. Additional liner material may be fed into the vessel as room is created by the removal of matured larvae and the corresponding cavities. Further, discrete cavities may help prevent disease or contaminant in one population from affecting any of the other populations within the same rearing container.

The example rearing container may also include, or be served by, one or more tubes or pipes arranged to dispense food, water, or air to each of the cavities individually. Thus, the rearing container may provide a robust environment in which to raise insect larvae populations before they mature into pupae, while reducing risks to each individual population from contaminants or other health issues. Further, different populations may be monitored for health and development within the individual cavities more easily than in a single large population of larvae, while retaining a form factor that enables increased density of insect larvae in a breeding facility.

This illustrative example is given to introduce the reader to the general subject matter discussed herein and the disclosure is not limited to this example. The following sections describe various additional non-limiting examples and examples of insect rearing containers.

Referring now to FIG. 1, FIG. 1 shows an example insect rearing container 100 having a walled vessel 110 with a liner 120 laid within the interior volume of the vessel 110. The walled vessel 110 in this example is formed from a hard plastic material that is substantially opaque. It should be appreciated, however, that a suitable vessel according to this disclosure may be transparent or translucent. Such vessels may allow for the application of light and dark cycles to the contents of the vessel, which may aid in developing circadian rhythms in insect larvae maturing in the container 100. While the walled vessel 110 shown in FIG. 1 has four walls and a base having a rectangular shape, any suitable shape may be employed, such as squares, circles, ovals, etc. Further, while the walls of the walled vessel 110 are formed, along with the base, as a contiguous piece, in some examples, one or more walls may be removable from the vessel.

The liner 120 is constructed of a suitable liner material, such as a polyethylene terephthalate ("PET") or other plastic, or a paper-based material. In some examples, however, suitable liner materials may be semi-rigid or rigid materials formed into a suitable shape. Such semi-rigid or rigid materials may include mesh materials, such as screens formed from plastic or metal. For example, in some examples, the liner 120 may be a container inserted within the vessel, such as a second vessel constructed of mesh material that may be laid within the vessel. Suitable materials should provide moisture barriers to prevent water or food from leaking through the liner material, and should not give off plasticizers or other noxious chemicals that might damage or kill the insect larvae. Though in some examples, a portion of a liner may be semi-permeable to allow exchange of material external to the vessel. For example, the vessel may be constructed with an integrated mesh material, such as a tray having one or more openings formed in the side of the vessel, and into which a mesh material (e.g., a fine mesh or a coarse mesh) is inserted. A liner in such an example does not cover the entirety of the interior of the vessel, but only serves as a filter for the vessel to enable movement of material, such as water, chemicals, bacteria, etc., into or out of the vessel. Thus, the liner has a shape corresponding to a shape of the interior surface, e.g., the side wall and opening in this example, and helps establish a cavity within the vessel by providing a semi-permeable barrier over the opening formed in the side of the vessel. Further, multiple liners may be employed in some examples, such as to enable exchange of material into and out of the vessel using a semi-permeable liner material, while providing an impermeable liner along the bottom of the vessel.

In this example, the liner 120 is laid across the interior volume of the walled vessel 110 and at least a portion of the walls of the vessel 110 to provide a cavity in which fluid (e.g., water,), insect larvae, food, etc. may be contained without escaping out of or through the liner 120. Thus, while the vessel 110 provides structural support for the liner 120, the liner 120 provides the boundaries of the liquid environment for the insect larvae. In this example, the liner 120 provides a single cavity in which the insect larvae will mature, however, other examples, as will be discussed in more detail below, provide multiple different cavities.

Figure 2A:
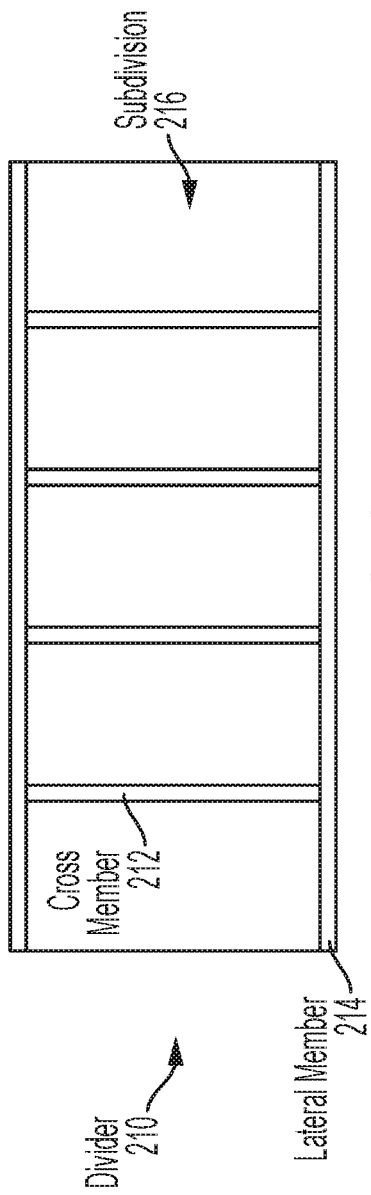
FIG. 2A shows an example divider assembly.
Figure 2B:
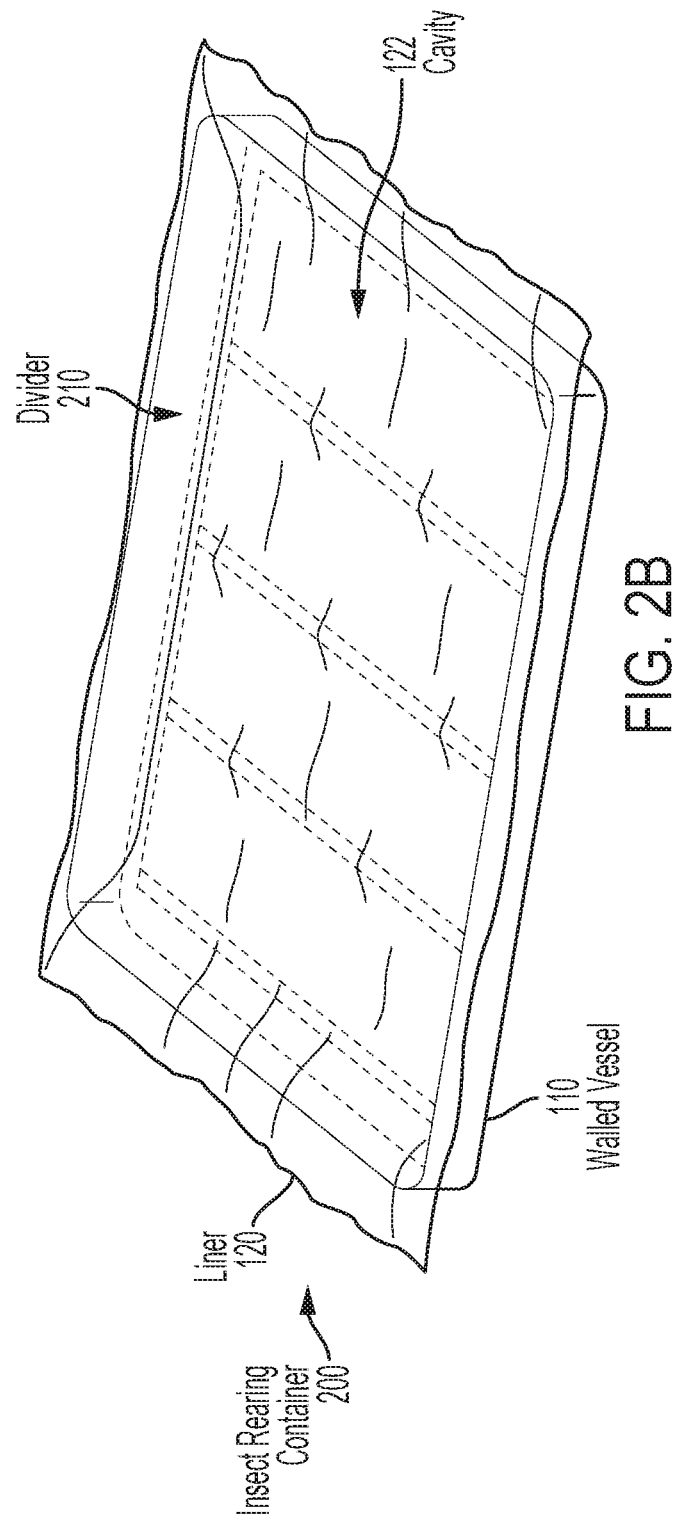
FIG. 2B shows an example insect rearing container with a divider assembly.

Referring now to FIGS. 2A-2B, FIG. 2A shows an example divider 210 for an insect rearing container. The divider 210 includes multiple cross members 212 connected between two lateral members 214 to form a ladder-like structure. In this example, the cross members 212 are rigid, while the lateral members 214 are flexible. For example, the cross members 212 may be wooden or metal bars, while the lateral members 214 may be rope or string. However, in some examples, any combination of rigid or flexible members may be employed for either or both of the cross members 212 or the lateral members 214. Further, while the example divider 210 shown in FIG. 2A provides five subdivisions 216 using four cross member 212, any suitable number of cross members 212, including only one cross member 212 to provide two subdivisions, may be used.

The cross members 212 in this example have a circular cross-section with a diameter of approximately 2 centimeters ("cm"); however, any suitable cross-section size or shape may be employed. The size may be selected based on a desired depth of fluid within an insect rearing container. For example, if a fluid depth of 1 cm is desired, cross member size may be selected to be double the fluid height. Alternatively, a fixed offset may be selected, e.g., cross members 212 may be sized to be 2 cm greater than whatever desired fluid depth is selected.

FIG. 2B illustrates an insect rearing container 200 in which the divider 210 is inserted into the walled vessel 110 shown in FIG. 1. As can be seen, the divider 210 has been laid within the interior volume of the walled vessel 110 and the liner 120 has been laid over the divider 210, creating discrete cavities 122 in the subdivisions 216 of the divider 210 between the cross members 212. Thus, in this example, multiple different, discrete insect larvae populations may be maintained within in a single vessel 110. And while in this example, the divider 210 is a separate component from the walled vessel 110 that may be removed from the walled vessel 110, in some examples, dividers 210 may be integrally formed on the vessel. For example, one or more walls or ridges may be formed on the base of the vessel to provide subdivisions within the vessel. A liner 120 may then be inserted into the vessel and laid over the dividers to create multiple cavities on the liner 120.

While in this example, the liner 120 is laid over the top of the divider, in some examples, the divider 210 may be positioned on top of the liner 120. For example, a divider, such as divider 210, may be laid on top of the liner 120 to provide subdivisions on top of the liner 120. To provide a fluid barrier, the divider may be constructed from a dense or heavy material, such as a metal or plastic, or may be affixed to the vessel using a coupling mechanism, such as a magnetic strip running the width or length of the vessel, or by applying one or more clamps to hold the divider tightly against the liner 120 and vessel. Or in some examples, the cross members 212 may be filters or otherwise have pores to allow exchange of fluid or chemicals between different cavities, while preventing larvae from migrating from one cavity to another. For example, the cross members 212 may be include a fine mesh or a porous cloth or paper material. Thus, if fresh water is introduced to one cavity, it may progress to other cavities by transuding the filters, which prevent other larger materials, such as the larvae or food, from moving to a different cavity. Further, the cross members 212 may in some examples have different filtering capabilities. For example, one cross member may have a fine mesh to only allow water and small chemicals through, while a second cross member may have a coarser mesh or other material to allow movement of water, chemicals and bacteria. Thus, different types of filtering materials may be employed in a single vessel to enable controlled movement of different materials into different cavities.

Figure 3A:
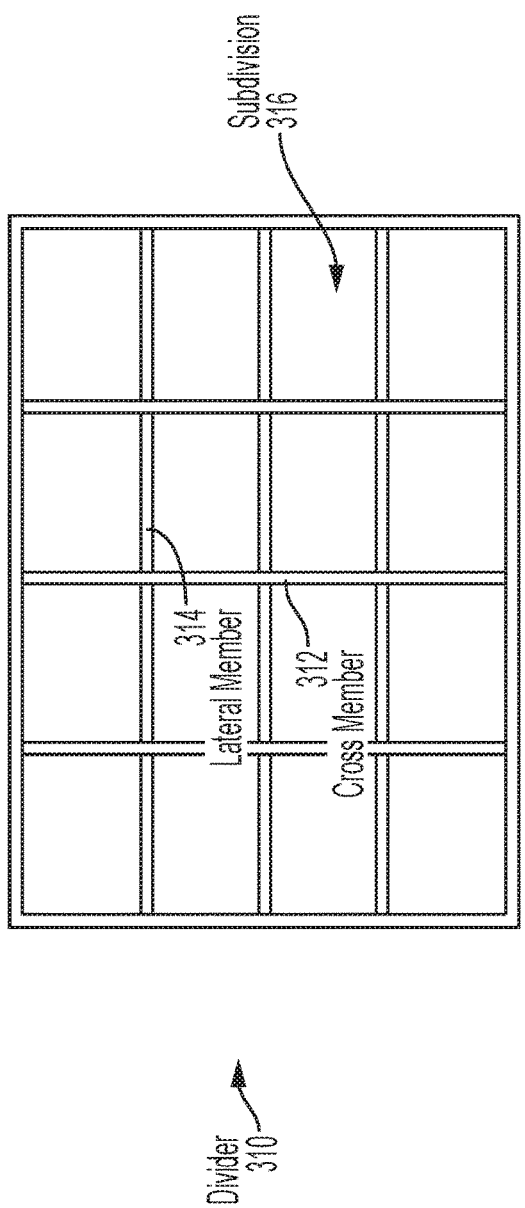
FIG. 3A shows an example divider assembly.
Figure 3B:
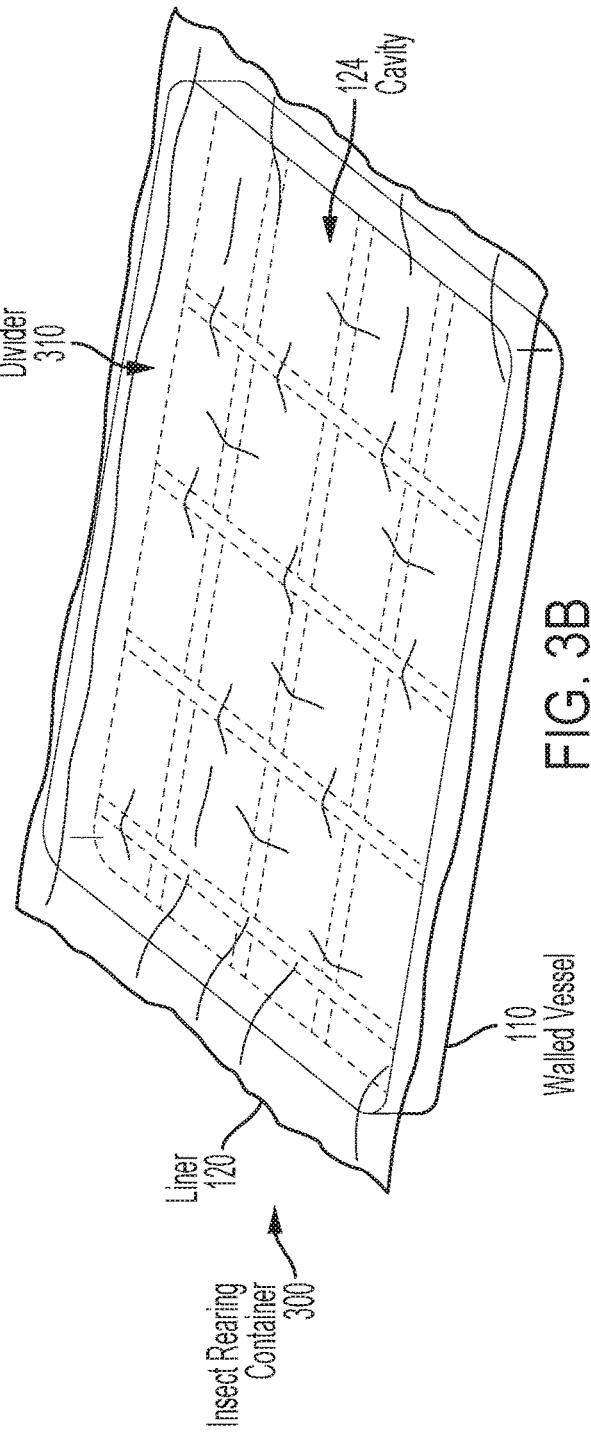
FIG. 3B shows an example insect rearing container with a divider assembly.

Referring now to FIGS. 3A-3B, FIG. 3A shows another example divider 310. In this example, the divider 310 defines a two-dimensional grid structure of subdivisions 316 defined by the cross and lateral members 312, 314. In this example, the cross and lateral members 312, 314 are each made of rigid material that are rigidly coupled to form a rigid structure. However, in some examples, the cross or lateral members 312, 314, may be formed of semi-rigid or flexible materials, such as plastic, rope, hollow tubing, etc. to define the subdivisions 316, or with flexible couplings to allow the cross or lateral members 312, 314 to move with respect to each other. Such example arrangements may allow the divider to be partially removed (or installed) within vessel to enable different populations of insect larvae to be extracted (or introduced) at different times without disturbing other larvae populations.

FIG. 3B shows an insect rearing container 300 where a walled vessel 110 has the divider 310 of FIG. 3A laid within the vessel's interior volume. The liner 120 has been laid over the top of the divider 310 and formed multiple discrete cavities 124 within the subdivisions of the divider 310. In this example, the liner 120 forms four rows of four cavities per row. Discrete populations of insect larvae may be introduced to each of the cavities 124, either at substantially the same time, or at different times to enable a staggered time-to-mature for each population. For example, new larvae populations may be introduced to the four right-most cavities 124 on day 1, along with water and food. On day 2, new larvae populations, food, and water may be introduced to the next four cavities 124. The progression may continue on successive days until all sixteen cavities have been filled. Because larvae populations were introduced over several days, the different populations may mature into pupae in the same sequence. Thus, as larvae populations pupate, they may be individually extracted (or extracted by row) from the respective cavity or cavities without substantially disturbing the other larvae populations.

As discussed above with respect to FIG. 2B, the liner 120 may be laid over the divider 310 in some examples, or the divider 310 may be laid over the liner 120 in some examples, so long as a fluid barrier is maintained between the discrete cavities 124. Alternatively, one or more of the cross or lateral members 312, 314 may include filters or pores to allow water or chemicals to be exchanged between the cavities, while preventing the exchange of food or larvae.

Figure 4:
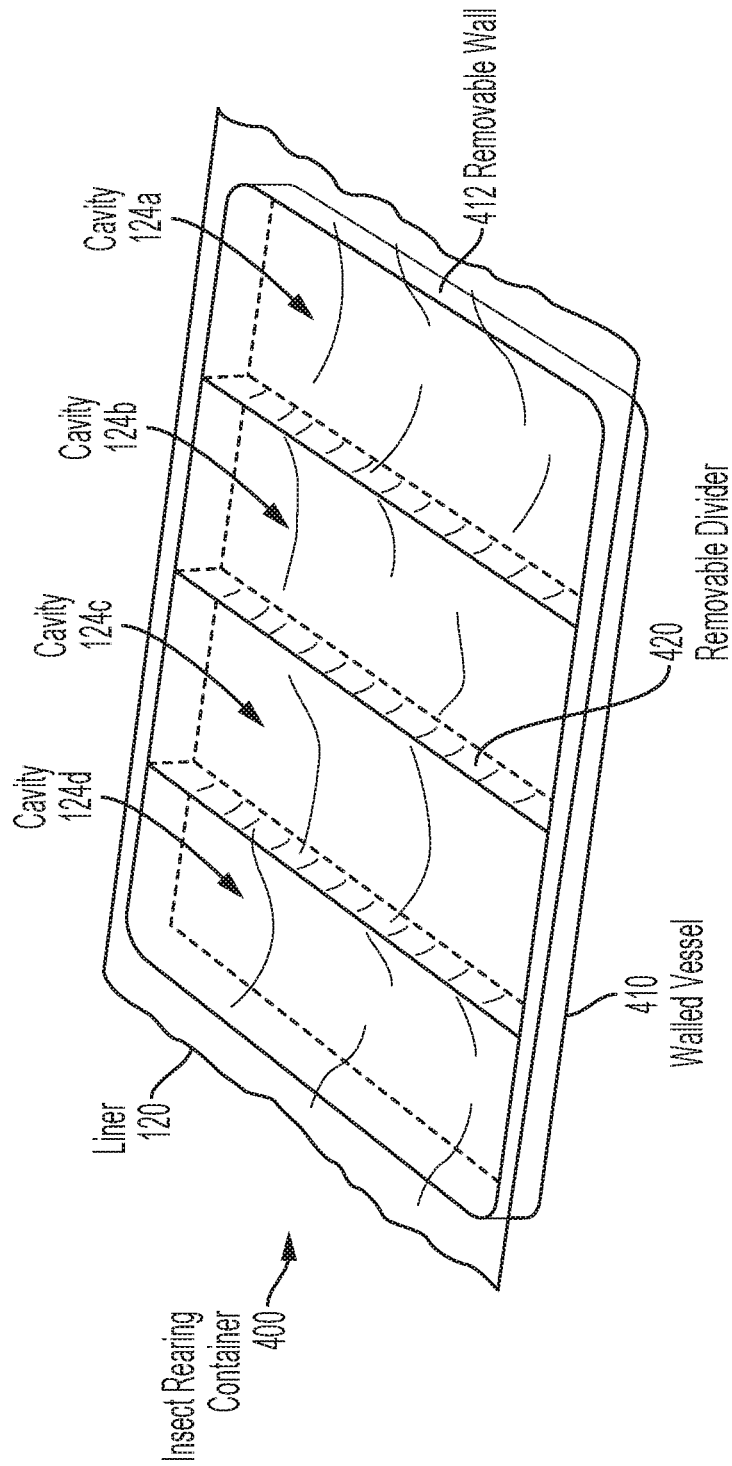
FIG. 4 shows an example insect rearing container.

Referring now to FIG. 4, FIG. 4 shows an example insect rearing container 400 that includes a walled vessel 410 with multiple dividers 420, over which is laid a liner 120 to form cavities 124a-d. The dividers 420 in this example retractable walls that may be inserted from the underside of the walled vessel 410 upward into the interior volume of the walled vessel 410. In some examples, however, the dividers 420 may be inserted into slots formed in the sides or base of the walled vessel 410 to define subdivisions within the interior volume, such as described above with respect to FIGS. 2A-3B. The dividers 420 enable the creation of discrete cavities 124a-d in the liner 120 when it is laid over the walled vessel 410 and the dividers 420, generally as described above.

Unlike the walled vessel 110 shown in FIG. 1, the example walled vessel 410 has a removable wall 412 that may enable easier removal of the contents of various cavities within the walled vessel. For example, if each of the cavities 124 has an insect population, removal of each discrete population may be accomplished by first removing the removable wall 412, and then emptying the contents of cavity 124a into a container. After contents of cavity 124a have been emptied, the divider 420 between cavity 124a and cavity 124b may be removed, allowing the contents of cavity 124b to be emptied into another container. This process may be repeated until each of the cavities 124a-d has been emptied into a separate container. Further, in some examples, the liner material may have perforations to enable a portion of the liner to be removed after a corresponding cavity has been emptied, which may allow other cavities to be emptied without being contaminated by materials from other cavities, or may allow additional liner material to be fed into the vessel to create new cavities, after one or more cavities have been emptied.

While the example shown in FIG. 4 includes removable dividers 420 running parallel to the removable wall, in some examples, the removable dividers 420 may be oriented to be perpendicular to the removable wall 410. Such an arrangement may allow the different cavities to be emptied into different containers substantially simultaneously. Further, in some examples, multiple removable dividers may be placed to create a grid of subdivisions within the walled vessel 410, similar to the example shown in FIGS. 3A-3B.

Figure 5:
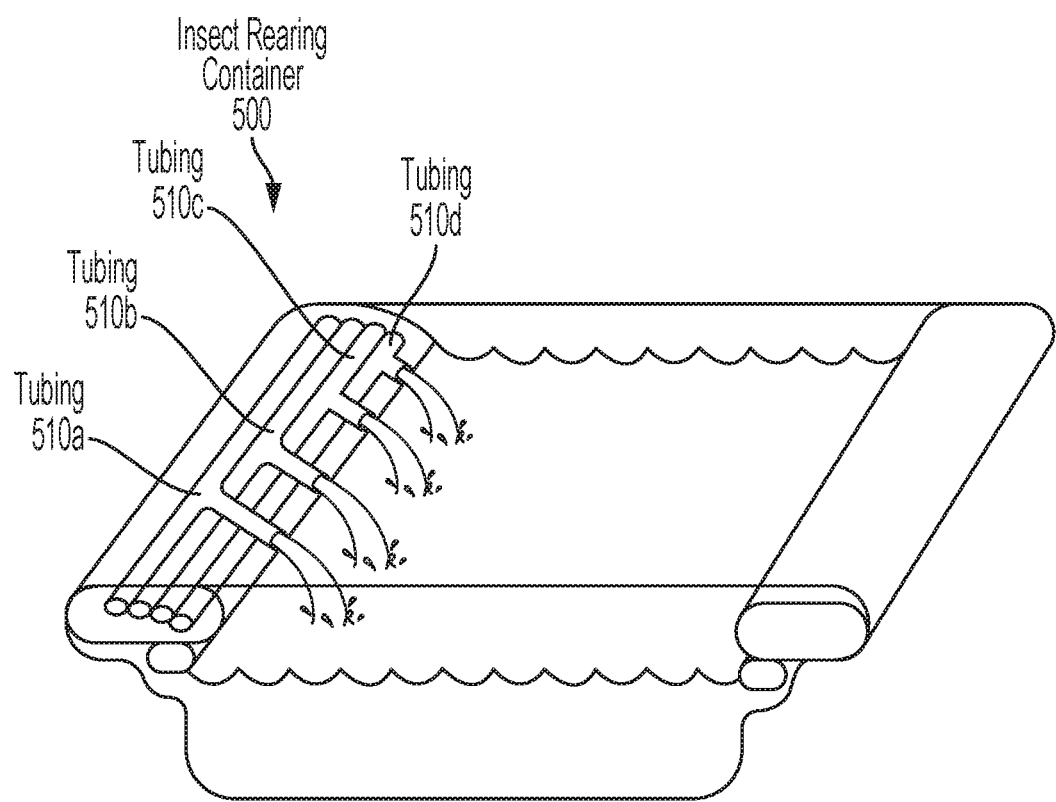
FIG. 5 shows an example insect rearing container having sets of tubing to distribute material into the insect rearing container.

Referring now to FIG. 5, FIG. 5 shows an example insect rearing container 510 defining a cavity in which an insect larvae population may be maintained. This example container 510 is served by multiple sets of tubing 510a-d that can supply different materials to the cavity. In this example, tubing 510a carries fresh water from a reservoir and provides the water to the cavity via an outlet from the tubing 510a. The other tubing 510b-d provides food or other materials. In some examples, tubing may circulate air across the surface of the cavity, or may include an outlet that is routed beneath the surface of any fluid within the cavity to provide air to the fluid itself. Thus, insect rearing containers may be able to provide fresh food, water, and air via tubing routed to one or more of the cavities within the container 500 itself. Tubing may be any suitable tubing or piping, rigid or flexible, usable to transport material from a source and to dispense the material into one or more cavities of an insect rearing container.

Figure 6A:
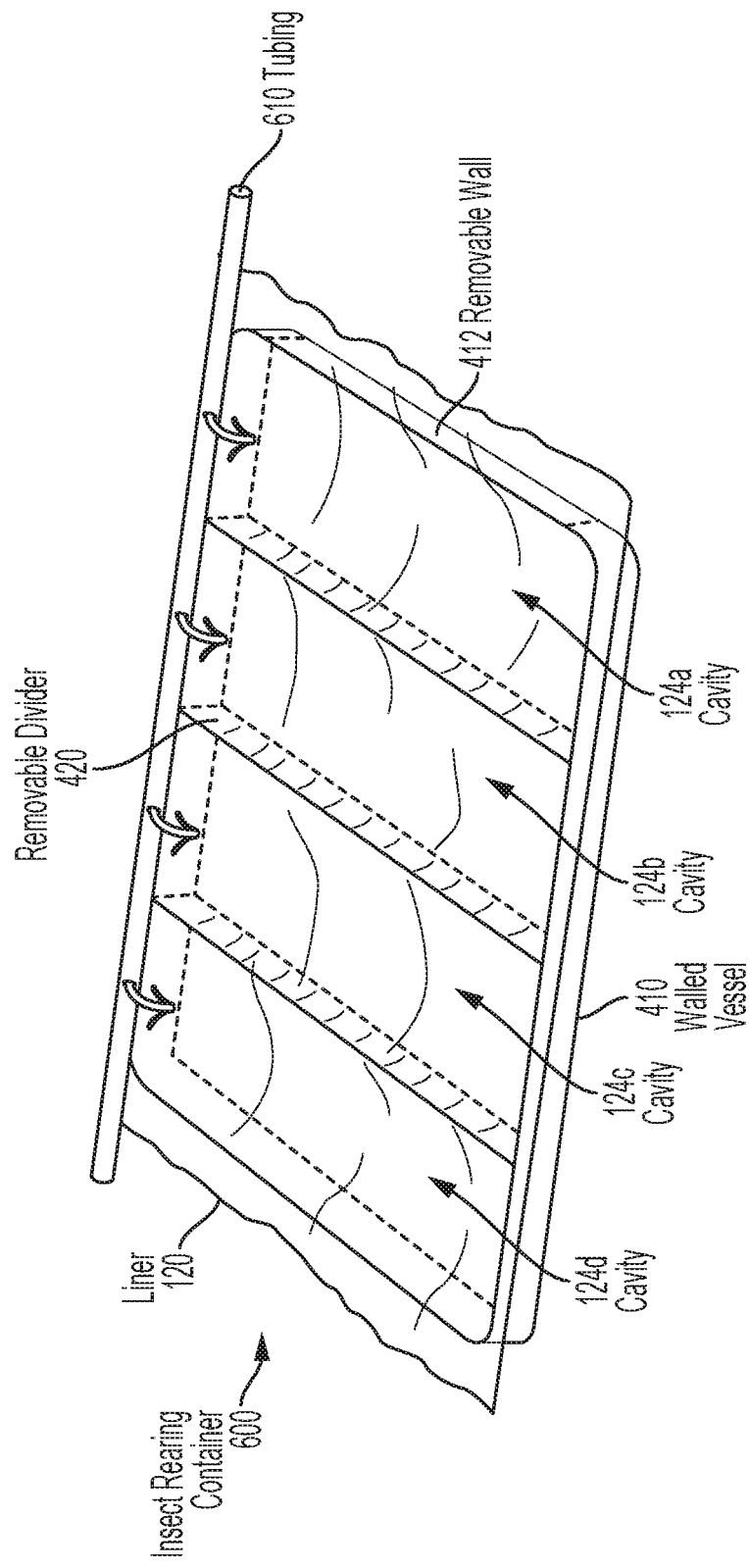
FIGS. 6A-6B show example insect rearing containers having tubing to distribute material into the insect rearing container.
Figure 6B:
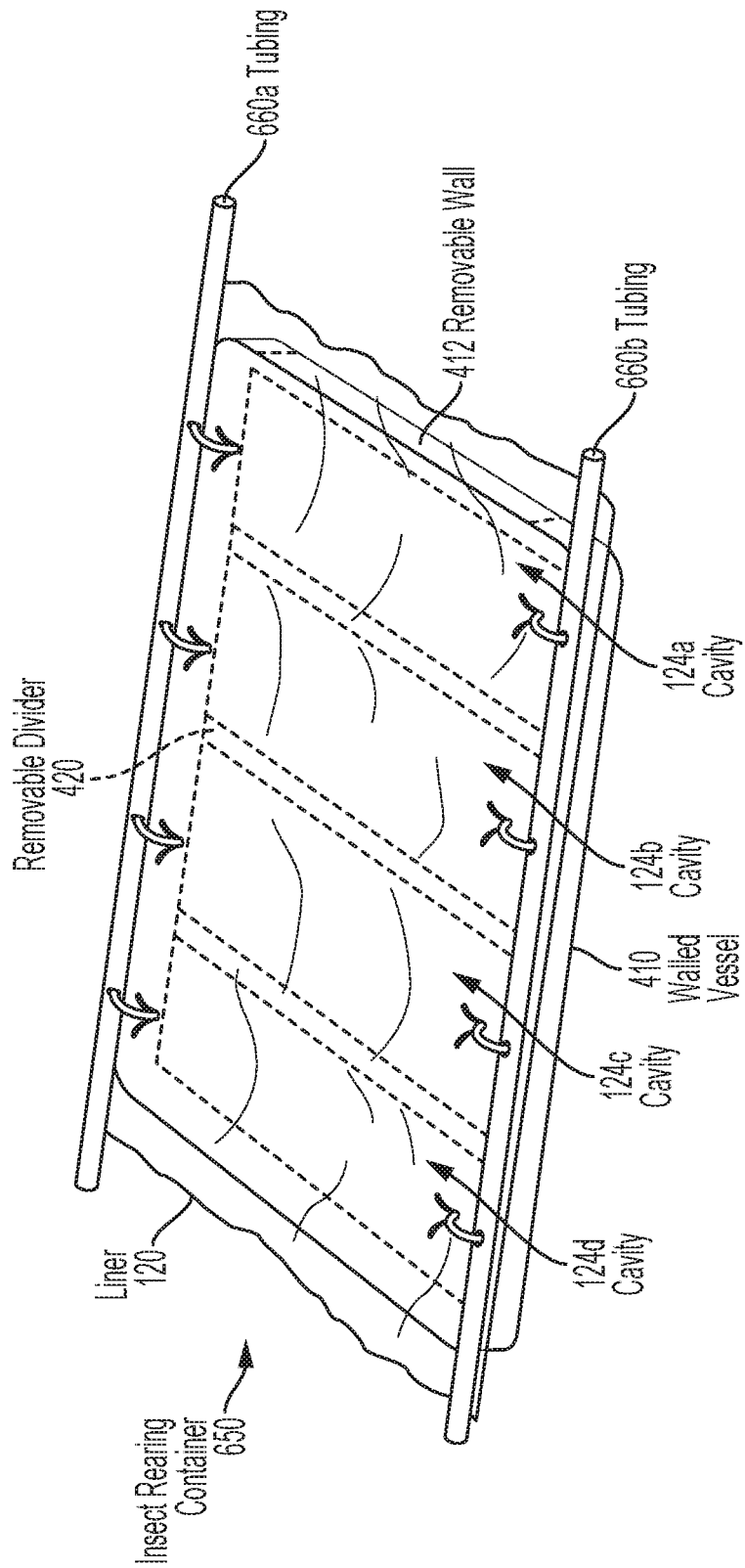

Referring now to FIGS. 6A-6B, FIGS. 6A-6B show example insect rearing containers 600, 650 having tubing to provide materials to cavities defined within the containers 600, 650. FIG. 6A shows an insect rearing container 600 that has a walled vessel with multiple removable dividers 420, over which is laid a liner 120 to define multiple cavities 124*a-d*. In addition, a length of tubing 610 has been routed across the cavities 124*a-d*. The tubing 610 that has openings to allow material to be distributed from the tubing 610 into the cavities 124*a-d*. Suitable materials could be water, food, air, etc. For example, air may be circulated over the cavities 124*a-d*, which may allow multiple containers 600 to be stacked on top of each other in close proximity without depriving insect larvae of needed fresh air. Other materials, such as water and food, may be distributed via the tubing, which may enable easier distribution of such materials to the cavities 124*a-d*. Further, if multiple such containers 600 are stacked on top of each other, or otherwise stored in large numbers, the use of tubing 610 to distribute such materials may substantially reduce the need to manually feed the larvae or manually provide fresh water.

FIG. 6B shows another example insect rearing container 650. This example container is similar to container 600 shown in FIG. 6A, but this example includes two different sets of tubing 660*a-b*, each of which can distribute a different material to the various cavities 124*a-d*. For example, tubing 660*a* could provide fresh water, while tubing 660*b* could provide food or air. While this example shows two different sets of tubing 660*a-b*, further examples may include more than two sets of tubing, such as shown in FIG. 5, to distribute multiple different types of material to the various cavities 124*a-d*.

Figure 7:
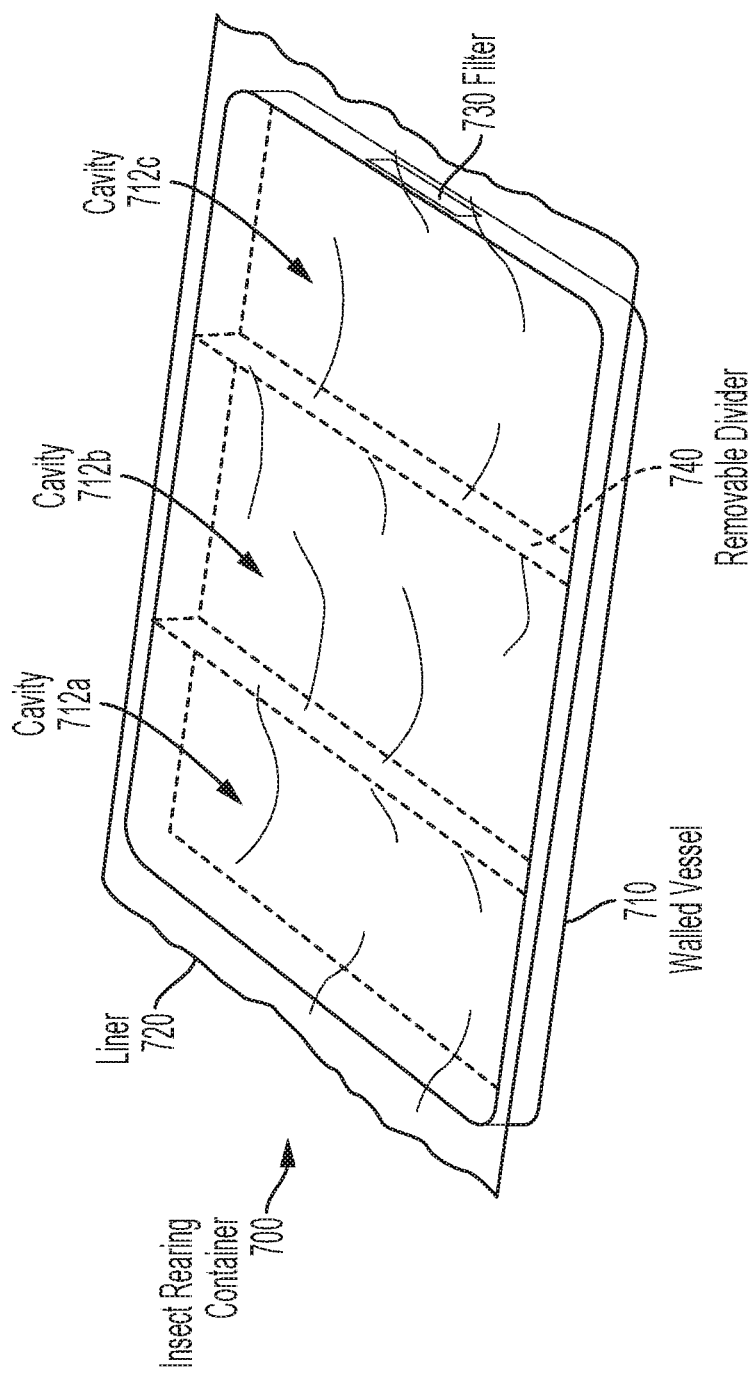
FIG. 7 shows an example insect rearing container having a filter and filtered dividers.

Referring now to FIG. 7, FIG. 7 shows an example insect rearing container 700. The insect rearing container 700 includes a walled vessel 710 forming an interior volume, in which is laid a liner 720. Multiple removable dividers 740 have been inserted into the walled vessel 710 on top of the liner to create multiple cavities 712*a-c*.

In this example, the liner 720 has been constructed of a suitable liner material, as discussed above, and has a filter 730 integrated into it. The filter 730 is sized to mate with and seal an opening in the walled vessel 710. The filter 730 is constructed to allow water or other fluid to pass through the filter 730, while preventing other particulates, such as larvae, waste, or food, from passing through it. In addition to the filter 730, each of the removable dividers 740 provides a filter to allow fluid to pass between the cavities 712*a-c*, while preventing waste materials, food, or larvae from exiting a respective cavity. The filter may be created using a mesh or an otherwise porous material as at least part of the removable dividers 740. Thus, the filter 730, in conjunction with the removable dividers 740, enables fresh water to be supplied to the cavities 712*a-c* while larvae populations are maturing, but without manually adding fresh water to each individual cavity 712*a-c*. In some examples, example insect rearing container 700 may also be equipped with one or more sets of tubing, such as illustrated in FIGS. 5-6B, to provide materials to the various cavities 712*a-c*.

Figure 8:
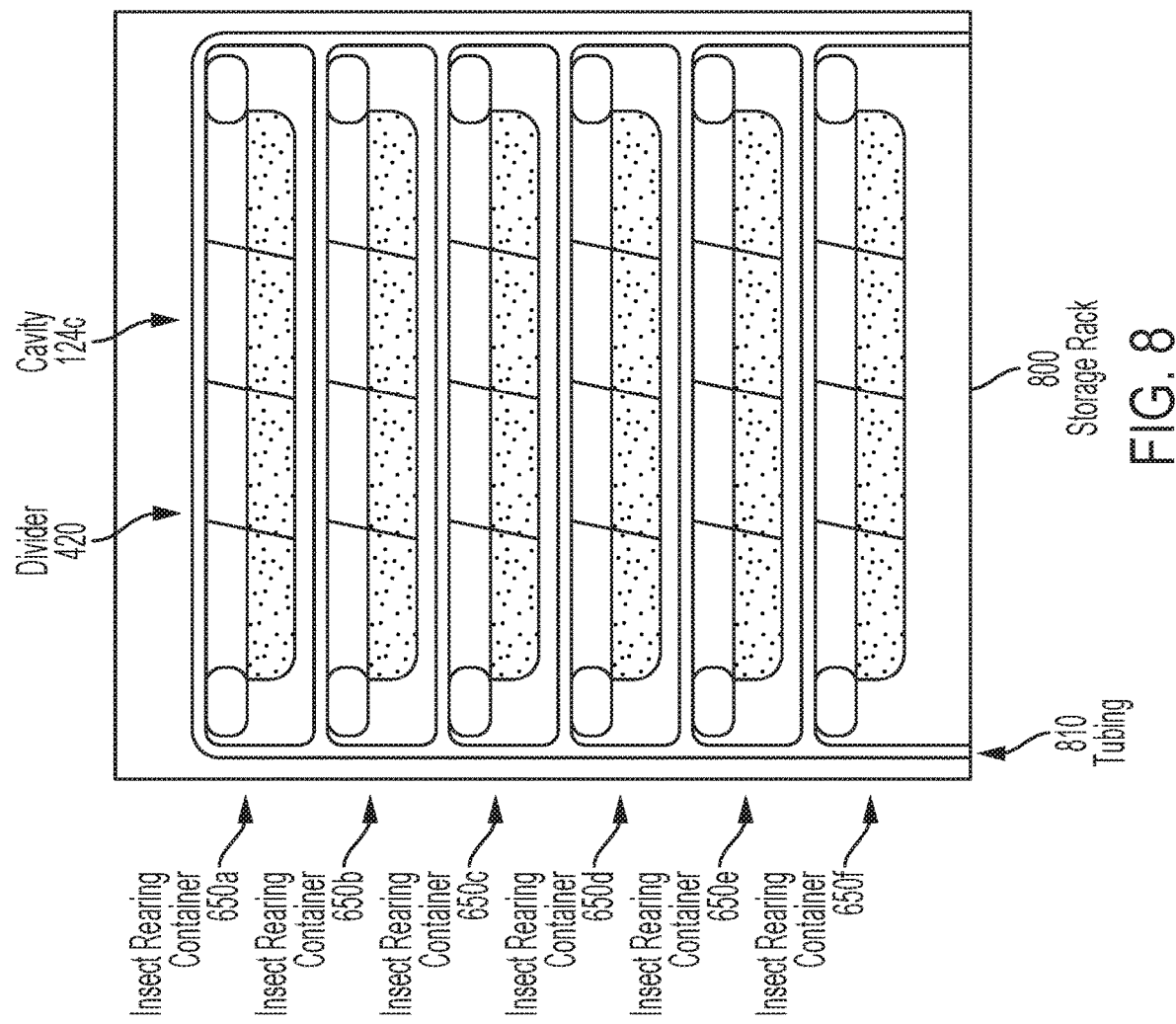
FIG. 8 shows an example storage rack that stores multiple insect rearing containers and provides tubing to distribute material into the respective insect rearing containers.

Referring now to FIG. 8, FIG. 8 illustrates an example storage rack 800 that has multiple insect rearing containers 650*a-f* stored within it. This example employs the insect rearing containers 650*a-f* shown in FIG. 6B; however, any suitable insect rearing container according to this disclosure may be employed. In addition, tubing 810 is routed over each of the insect rearing containers 650*a-f* to provide material, such as food, water, or air, to each of the containers. And while only one set of tubing 810 is shown in this example, multiple sets of tubing, such as illustrated in FIGS. 5-6B may be employed according to different examples.

The configuration shown in FIG. 8 may provide an advantage in storage density. Some examples of insect rearing containers, such as those described above, may be stored in high densities, such as stacked on top of each other, to increase the number of insect larvae being reared in a particular location. As discussed above, a vessel with a liner, including with multiple dividers, is taller than the fluid level stored in one or more cavities formed in the liner. Thus, one vessel may be stacked on top of the other, while maintaining an air gap between the fluid in the lower vessel and the base of the upper vessel. In some examples, an air gap of at least 1 cm may be desirable, though smaller gaps, such as 0.5 cm or less may be employed. Further, if tubing is employed, such as described above with respect to FIGS. 5-6B and 8, or filters are employed, such as described with respect to FIG. 7, fresh water, food, or air may be supplied to larvae populations within each cavity without a worker manually pouring materials into the respective cavities. Thus, a suitable rearing environment may be established and maintained in a large number of individual rearing containers stored in high density stacks.

Figure 9:
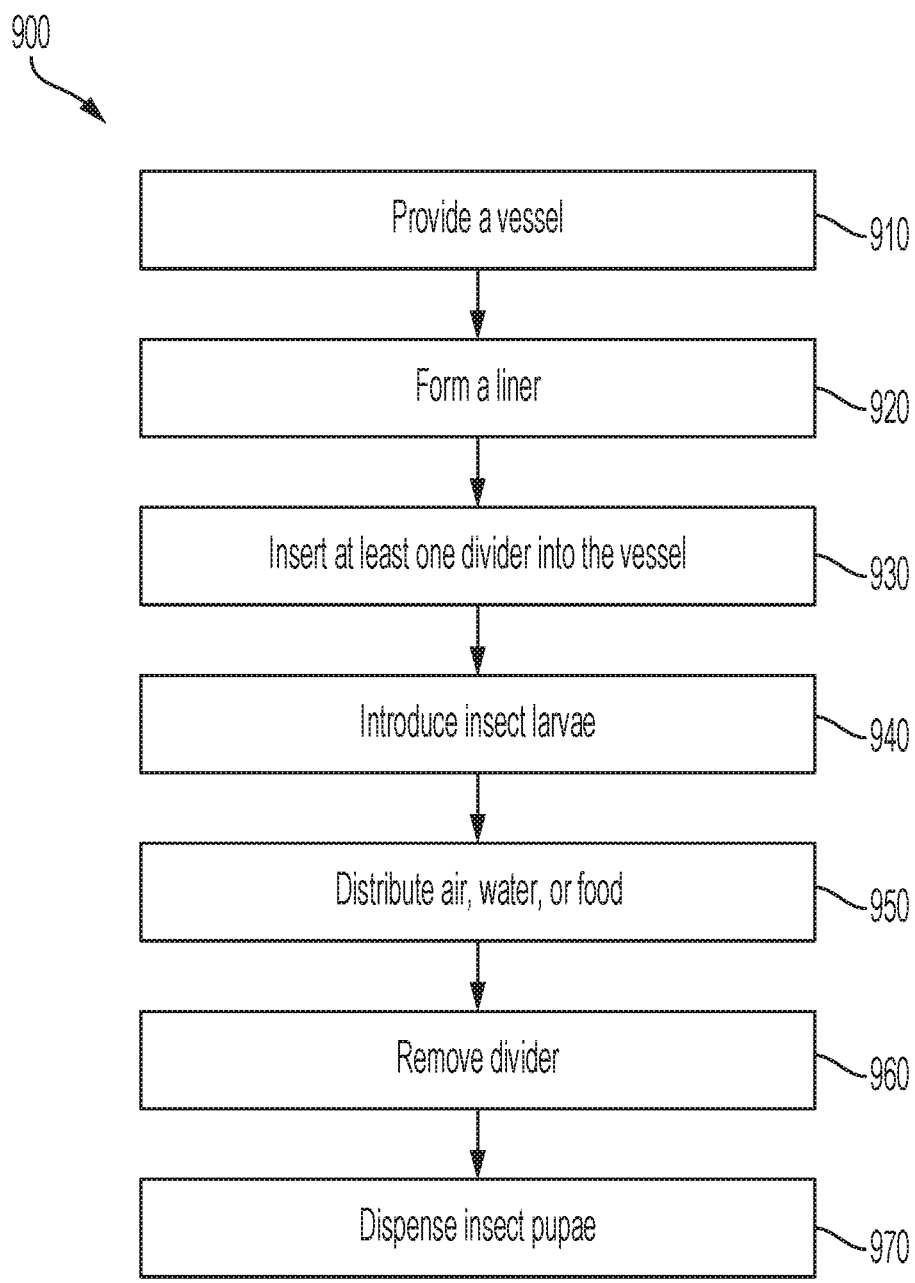
FIG. 9 shows an example method for providing an insect rearing container.

Referring now to FIG. 9, FIG. 9 shows an example method 900 for providing an insect rearing container. The example method 900 will be described with respect to the example insect rearing container 600 shown in FIG. 6A; however any suitable insect container according to this description may be employed, including any of those described with respect to FIGS. 1-5, 6B and 7.

At block 910, a vessel 410 is provided. Any suitable vessel may be employed, such as discussed above with respect to FIGS. 1-8.

At block 920, a liner 120 is formed and laid within the vessel 410 to establish at least one cavity 124*a-d* within the vessel 410. Any suitable liner may be employed, such as discussed above with respect to FIGS. 1-8.

At block 930, one or more dividers 420 is inserted into the vessel 410. In this example, the dividers 420 are inserted beneath the liner 120 and may be inserted through the base of the vessel 410 and into the interior volume. Alternatively, the dividers 420 may be inserted into the interior volume and mated with a mounting feature, such as a groove, slot, magnet, or other mechanism to secure the dividers 420 into place. In this example, the dividers 420 are inserted before the liner 120 is formed and laid within the vessel 410; however, in some examples, the liner 120 may be laid within the vessel 410 before the divider(s) are inserted. After both the liner 120 and the dividers 420 have been positioned, respectively, cavities 124*a-d* are defined within the liner based on the positioning of the dividers.

At block 940, insect larvae are introduced into one or more of the cavities 124*a-d*. In this example, insect larvae are introduced into each of the cavities 124*a-d* at substantially the same time. However, as discussed above, in some examples, larvae populations may be introduced into different cavities at different times, such as on different days. By staggering the introduction of discrete larvae populations, each population may mature into pupae at different times, thus allowing pupae to be removed as they mature, in sequence.

At block 950, air, water, or food is distributed to each of the cavities 124*a-d*. In this example, an initial quantity of food and water is introduced into each cavity 124*a-d*. The tubing 610 may then be used to distribute additional food or water, or to circulate air above the cavities 124*a-d*. In some examples, multiple sets of tubing may be employed, such as shown in FIGS. 5 and 6B. Such examples may distributed different types of material using the different sets of tubing. In some examples, however, food or water may be poured directly into the cavities 124*a-d* from a container.

At block 960, a divider 420 is removed from the vessel 410. For example, removable wall 412 (which functions as a divider) maybe removed to allow the contents of cavity 124a to be dispensed. If cavity 124a has already been dispensed, the removable divider separating cavities 124a-b may be removed to allow the contents of cavity 124b to be dispensed. In some examples, some or all dividers may be removed at the same time, mixing the corresponding insect larvae populations, which may then be dispensed en masse into a single container. However, in some examples, however, the vessel may have permanent dividers, such as dividers integrally formed into the vessel. In such examples, a divider may not be removed.

At block 970, the contents of at least one cavity is dispensed into a container. For example, if an insect larvae population has matured into pupae, the insect pupae may be dispensed into a container.

It should be appreciated that multiple vessels may be queued in succession for execution of the method 700 (or other example methods according to this description). Thus, a single liner may be formed across multiple vessels to enable all of the vessels to move in unison through the remainder of the blocks of the process. Further, because these successive vessels may arrive at different stations in order, one may be processed to add insect larvae, while the next is processed to add food and water, and so forth. Similarly, in some examples where a vessel has multiple cavities, different cavities may be processed individually according to example methods. For example, with respect to the example shown in FIG. 7, the insect rearing container 700 may be processed according to an example method whereby cavity 712c has insect larvae introduced while cavity 712b (and 712a in this example) is formed by adding a divider to the walled vessel 710. Then the walled vessel 710 advances through a processing station and cavity 712c has food and water added to it, while cavity 712b has insect larvae introduced. The walled vessel 710 may advance again such that cavity 712b has food and water added to it, while cavity 712a has insect larvae introduced, and so forth. Further, this walled vessel 710 may be one of multiple walled vessels having a single sheet of liner material formed to be inserted as a continuous liner across the multiple walled vessels. Thus, a monolithic structure with multiple cavities constructed from a sheet of liner may be processed in an assembly-line fashion. Such a monolithic structure may be formed in a single vessel or across multiple vessels in some examples.

It should also be appreciated that the blocks described above are described in an example order and that different orderings are contemplated by this disclosure. Further, not all blocks may be performed in all example methods. For example, a vessel may have dividers integrally formed into it, thus blocks 930 and 960 may not be performed. Or in some examples, a vessel may not be subdivided and a single cavity within a liner may be formed in the vessel. Still further variations fall within the scope of this disclosure.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. An insect rearing system comprising:
a vessel comprising at least one interior surface defining a volume;
a liner comprising a liner material, the liner having a shape corresponding to a shape of the interior surface, the liner configured to be disposed within the volume to establish a cavity within which water, insect larvae, and insect larvae food may be disposed and maintained;
a divider disposed within the vessel, the divider configured to define a plurality of cavities within an interior of the vessel;
at least one tube arranged to distribute a substance to at least one of the one or more cavities; and
wherein the vessel defines an opening configured to receive the liner and to allow the liner to substantially conform to the shape of the interior surface.

2. The insect rearing system of claim 1, wherein the liner is disposed within the vessel and comprises:
a quantity of water,
a population of insect larvae; and
a quantity of food for the insect larvae.

3. The insect rearing system of claim 2, wherein the interior surface defines a lower surface of the volume and a side surface of the volume, wherein the side surface has a height of at least 0.5 cm greater than the depth of the water.

4. The insect rearing system of claim 1, wherein divider is placed on top of the liner within the vessel, wherein the divider is configured to divide the cavity into a plurality of discrete cavities.

5. The insect rearing system of claim 4, wherein the divider comprises a filter or defines at least one pore to enable an exchange of fluid or chemicals between at least two of the discrete cavities.

6. The insect rearing system of claim 5, wherein a size of the at least one pore is selected based on a substance or material to allow through the pore.

7. The insect rearing system of claim 5, wherein a first divider includes a first pore and a second divider includes a second pore, wherein the first pore and the second pore have different sizes.

8. The insect rearing system of claim 1, wherein the liner is disposed within the vessel and over the divider, wherein the divider is configured to divide the cavity into a plurality of discrete cavities.

9. The insect rearing system of claim 8, wherein the divider comprises a ladder structure having a plurality of rungs, wherein the liner is disposed over the ladder structure, each rung establishing at least in part a discrete cavity.

10. The insect rearing system of claim 8, wherein the divider defines a grid structure defining a two-dimensional array of openings, wherein the liner is disposed over the grid structure, each opening in the two-dimensional array establishing a discrete cavity.

11. The insect rearing system of claim 10, wherein the grid structure comprises plurality of first members and a plurality of second members, each of the first members substantially parallel to the other first members, each of the second members substantially parallel to the other second members, and each of the first members substantially perpendicular to each of the plurality of second members, wherein each of the first members and each of the second members may be individually inserted into or removed from the grid structure.

12. The insect rearing system of claim 1, wherein the substance comprises water.

13. The insect rearing system of claim 1, wherein the at least one tube comprises a plurality of tubes, each tube of the plurality of tubes positioned above the liner and to distribute the substance to a different subset of cavities of the plurality of cavities.

14. The insect rearing system of claim 1, wherein the at least one tube comprises a plurality of tubes, each tube of the plurality of tubes positioned above the liner and to distribute a different substance to at least some cavities of the plurality of cavities.

15. The insect rearing system of claim 14, wherein the plurality of tubes are configured to distribute at least two substances, the at least two substances comprising at least two of (i) water, (ii) air, or (iii) food, wherein each tube of the plurality of tubes delivers one of the at least two substances.

16. The insect rearing system of claim 15, wherein at least one tube is configured to distribute water and food.

17. The insect rearing system of claim 1, wherein the vessel defines a second opening in the interior surface, and wherein liner defines a filter opening, the filter opening and the second opening having corresponding shapes and sizes, and wherein the liner comprises a filter disposed within filter opening, the filter opening and the second opening coupled to allow the exchange of fluid from a fluid source external to the vessel with fluid disposed within the liner.

18. The insect rearing system of claim 1, wherein the vessel and the liner are transparent or translucent.

19. A method comprising:
providing a vessel comprising at least one interior surface defining a volume;
inserting a divider into the vessel to establish a plurality of cavities within an interior of the vessel;
forming a liner comprising a liner material within the volume and over the interior surface, the liner having a shape corresponding to a shape of the interior surface and establishing a cavity within which water, insect larvae, and insect larvae food may be disposed and maintained;
positioning at least one tube to distribute a substance to at least one cavity of the plurality of cavities; and
wherein the vessel defines an opening configured to receive the liner and to allow the liner to substantially conform to the shape of the interior surface.

20. The method of claim 19, wherein the liner is positioned above the divider.

21. The method of claim 20, wherein the divider defines a grid structure defining a two-dimensional array of openings, each opening in the two-dimensional array establishing a discrete cavity.

22. The method of claim 21, wherein the grid structure comprises plurality of first members and a plurality of second members, each of the first members substantially parallel to the other first members, each of the second members substantially parallel to the other second members, and each of the first members substantially perpendicular to each of the plurality of second members, wherein each of the first members and each of the second members may be individually inserted into or removed from the grid structure.

23. The method of claim 22, further comprising removing, in sequence, one or more first or second members from the vessel to dispense contents of at least one cavity into another vessel.

24. The method of claim 23, wherein each cavity is dispensed into a different vessel.

25. The method of claim 19, further comprising, distributing the substance to at least some cavities of the plurality of cavities.

26. The method of claim 19, wherein the substance comprises water.

27. The method of claim 19, wherein the at least one tube comprises a plurality of tubes, each tube of the plurality of tubes positioned above the liner and to distribute the substance to a different subset of cavities of the plurality of cavities.

28. The method of claim 20, wherein the at least one tube comprises a plurality of tubes, each tube of the plurality of tubes positioned above the liner and to distribute a different substance to at least some cavities of the plurality of cavities.

29. The method of claim 28, wherein the plurality of tubes are configured to distribute at least two substances, the at least two substances comprising at least two of (i) water, (ii) air, or (iii) food, wherein each tube of the plurality of tubes delivers one of the at least two substances.

30. The method of claim 29, wherein at least one tube is configured to distribute water and food.

31. The method of claim 29, further comprising, distributing water, air, and food using the plurality of tubes.

32. The method of claim 19, wherein the divider comprises a ladder structure having a plurality of rungs, each rung establishing at least in part a discrete cavity.

33. The method of claim 32, further comprising removing, in sequence, one or more rungs from the vessel to dispense contents of at least one cavity into another vessel.

34. The method of claim 33, wherein each cavity is dispensed into a different vessel.

* * * * *